(12) United States Patent
Del Giudice et al.

(10) Patent No.: US 6,841,155 B1
(45) Date of Patent: Jan. 11, 2005

(54) **IMMUNIZATION AGAINST AND TREATMENT FOR INFECTION BY *H. PYLORI***

(75) Inventors: Guiseppe Del Giudice, Siena (IT); Rino Rappuoli, Castelnuovo Berar (IT)

(73) Assignee: Chiron S.r.l., Siena (IT)

(*) Notice: Subject to any disclaimer, the term of this patent is extended or adjusted under 35 U.S.C. 154(b) by 0 days.

(21) Appl. No.: 09/674,393

(22) PCT Filed: Apr. 30, 1999

(86) PCT No.: PCT/IB99/00851

§ 371 (c)(1),
(2), (4) Date: Jan. 18, 2001

(87) PCT Pub. No.: WO99/57278

PCT Pub. Date: Nov. 11, 1999

(30) Foreign Application Priority Data

Apr. 30, 1998 (GB) .............................. 9809398
Sep. 25, 1998 (GB) .............................. 9820976

(51) Int. Cl.[7] .............................................. A61K 39/00
(52) U.S. Cl. ................ 424/184.1; 424/234.1; 424/236.1
(58) Field of Search ............... 424/184.1, 234.1, 424/236.1

(56) References Cited

U.S. PATENT DOCUMENTS

| | | | | |
|---|---|---|---|---|
| 5,217,898 A | * | 6/1993 | Kaslow et al. ............... | 435/255 |
| 5,859,219 A | | 1/1999 | Cover et al. | |
| 5,874,300 A | * | 2/1999 | Blaser et al. ................ | 435/325 |
| 5,891,432 A | * | 4/1999 | Hoo ........................ | 424/93.21 |
| 5,928,865 A | | 7/1999 | Covacci | |
| 6,013,463 A | | 1/2000 | Cover et al. | |
| 6,025,164 A | * | 2/2000 | Bolin et al. ................ | 435/69.3 |
| 6,054,132 A | | 4/2000 | Cover et al. | |
| 6,077,706 A | | 6/2000 | Covacci et al. | |
| 6,090,611 A | | 7/2000 | Covacci et al. | |
| 6,126,938 A | * | 10/2000 | Guy et al. ............... | 424/184.1 |
| 6,130,059 A | | 10/2000 | Covacci et al. | |

FOREIGN PATENT DOCUMENTS

| | | | |
|---|---|---|---|
| WO | WO 93/16723 | | 9/1993 |
| WO | WO 93/18150 | | 9/1993 |
| WO | 9318150 | * | 9/1993 |
| WO | WO 96/01272 | | 1/1996 |
| WO | WO 96/14393 | | 5/1996 |
| WO | 9614393 | * | 5/1996 |
| WO | WO 96/33274 | | 10/1996 |
| WO | WO 97/25129 | | 7/1997 |
| WO | WO 98/04702 A2 A3 | | 2/1998 |
| WO | WO 98/27432 | | 6/1998 |
| WO | WO 98/42375 A1 | | 10/1998 |
| WO | WO 99/65518 A2 | | 12/1999 |

OTHER PUBLICATIONS

Guy et al., Vaccine, vol. 16 (8), (1998), pp. 850–856.*
Manetti et al., Infection and Immunity, 63(11), (1995), pp. 4476–4480.*
Guy et al., "Systemic Immunization With Urease Protects Mice Against *Helicobacter Pylori* Infection," *Vaccine* 16(8):850–856 (1998).
Manetti et al., "*Helicobacter pylori* Cytotoxin: Importance of Native Conformation for Induction of Neutralizing Antibodies," *Infect. Immun.* 63(11):4476–4480 (1995).
Corthésy–Theulaz et al., "Mice are protected from Helicobacter pylori infection by nasal immunization with attenuated Salmonella typhiurium phoP$^c$ expressing urease A and B subunits," *Infection and Immunity* 66(2):581–586, 1998.
Guy et al., "Mucosal, systemic, or combined therapeutic immunizations in cynomolgus monkeys naturally infected with Gastrospirillum hominis–like organisms," *Vaccine Research* 6(3):141–150, 1997.
Kleanthous et al., "Rectal and intranasal immunizations with recombinant urease induce distinct local and serum immune responses in mice and protect against Helicobacter pylori infection," *Infection and Immunity* 66(6):2879–2886, 1998.
Kraehenbuhl et al., "Molecular and cellular basis of immune protection of mucosal surfaces," *Physiological Reviews* 72(4):853–879, 1992.

* cited by examiner

*Primary Examiner*—Marianne C. Seidel
*Assistant Examiner*—C. Delacroix-Muirheid
(74) *Attorney, Agent, or Firm*—Roberta L. Robins; Rebecca M. Hale; Robert P. Blackburn

(57) ABSTRACT

Methods for treating and/or protecting *H. pylori* infection are described. The methods utilize non-mucosal administration of an effective amount of one or more *H. pylori* antigens.

14 Claims, 15 Drawing Sheets

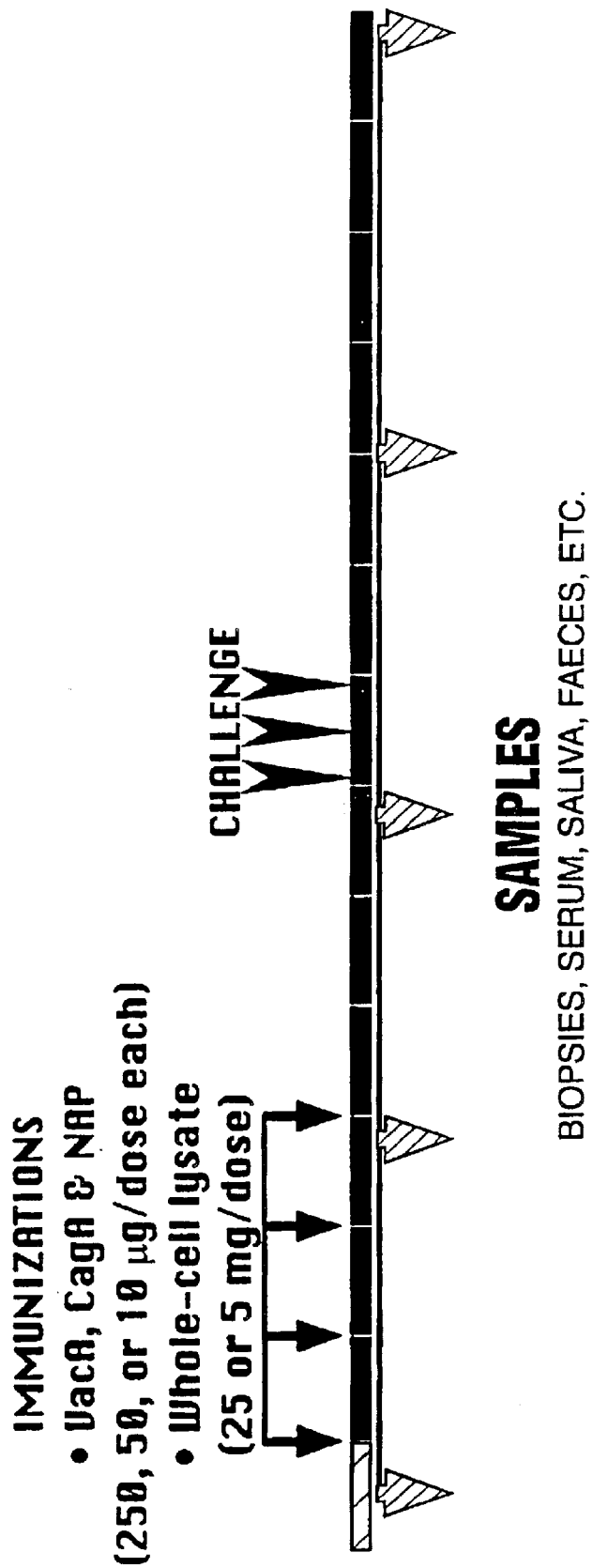

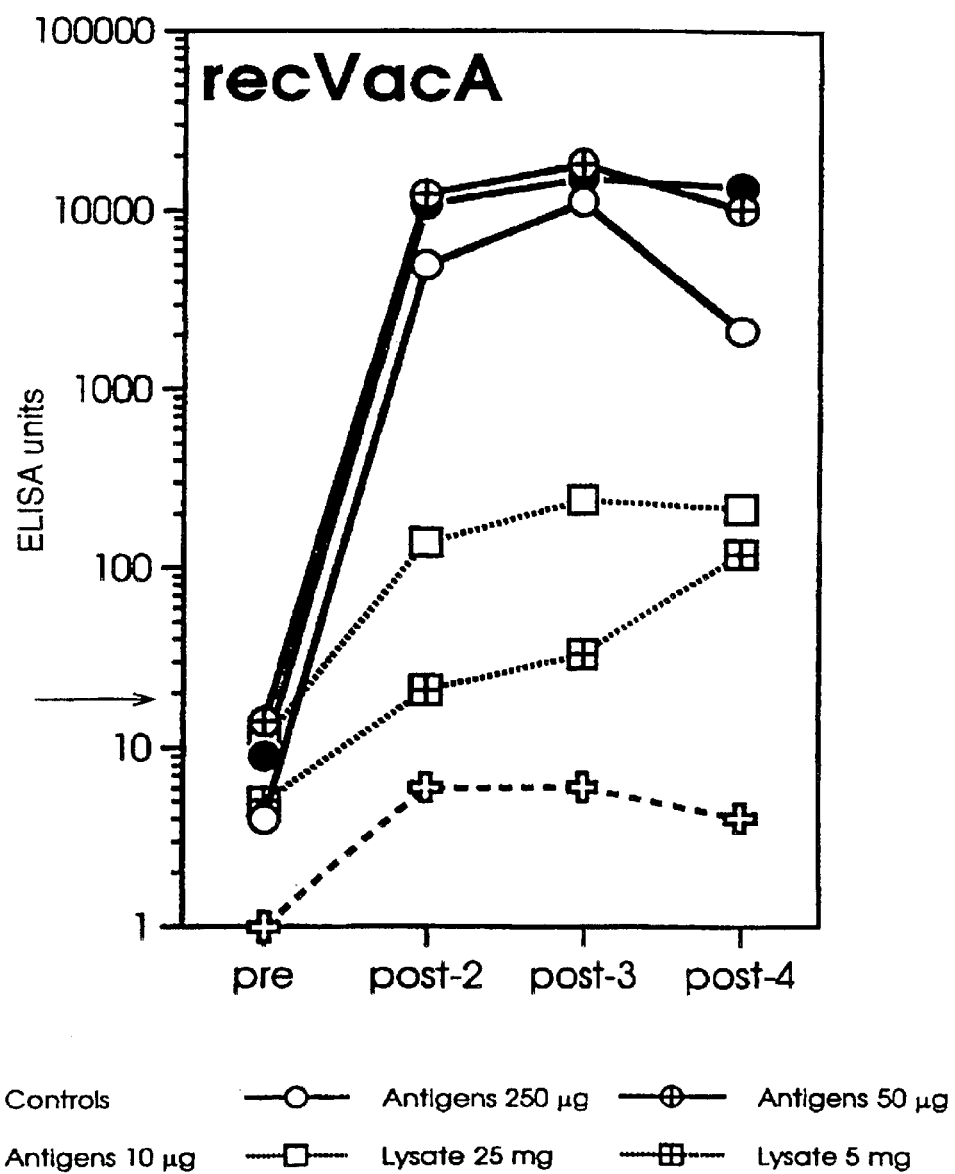

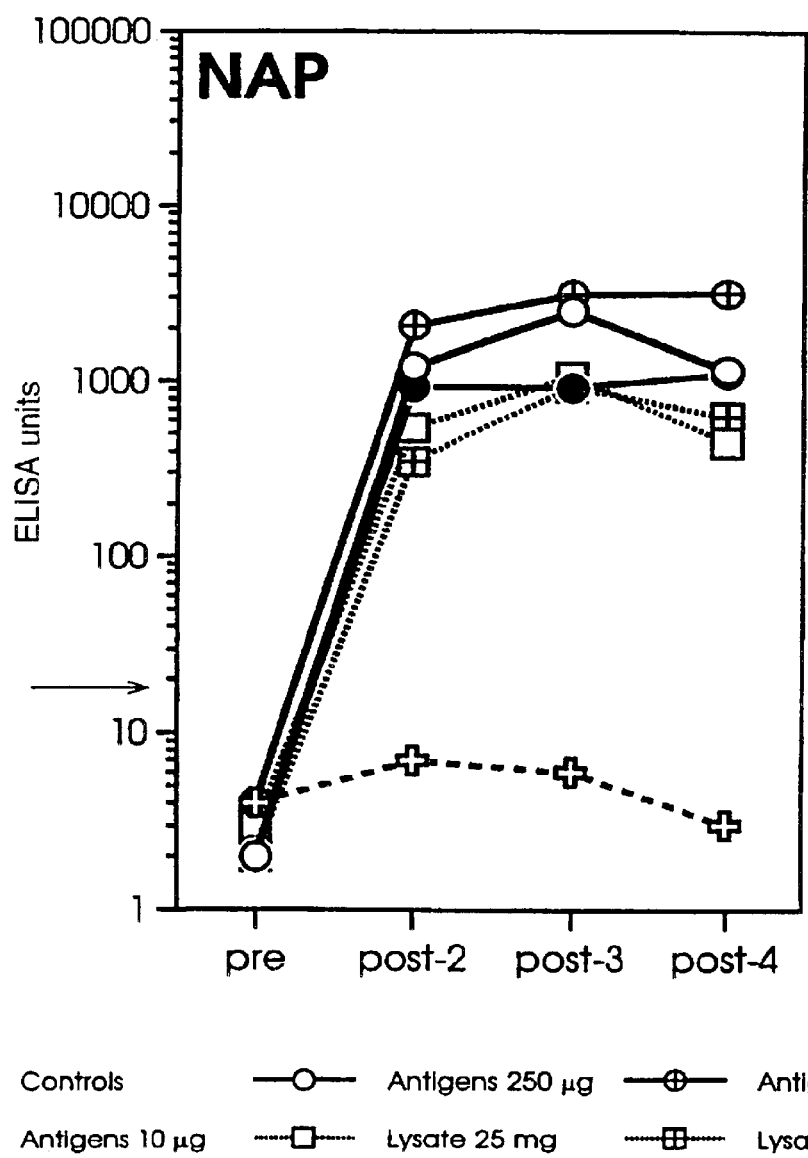

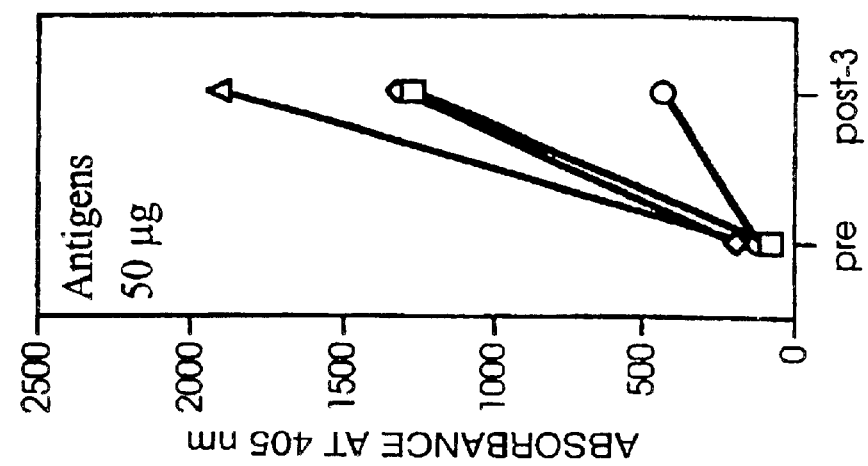
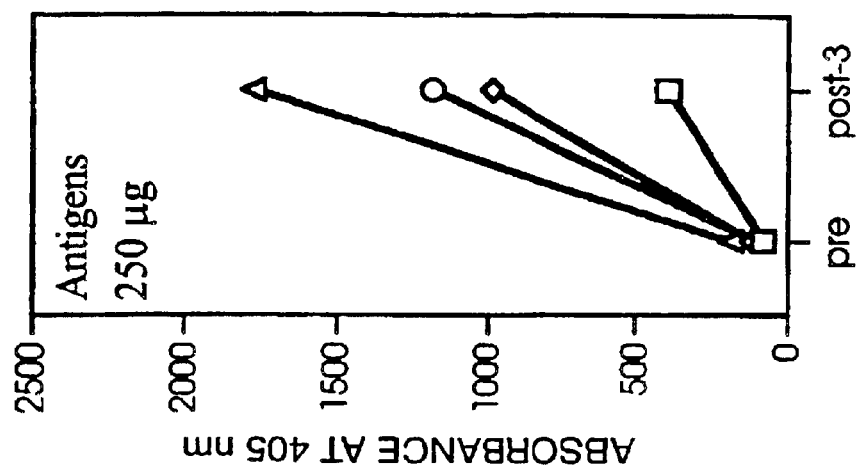
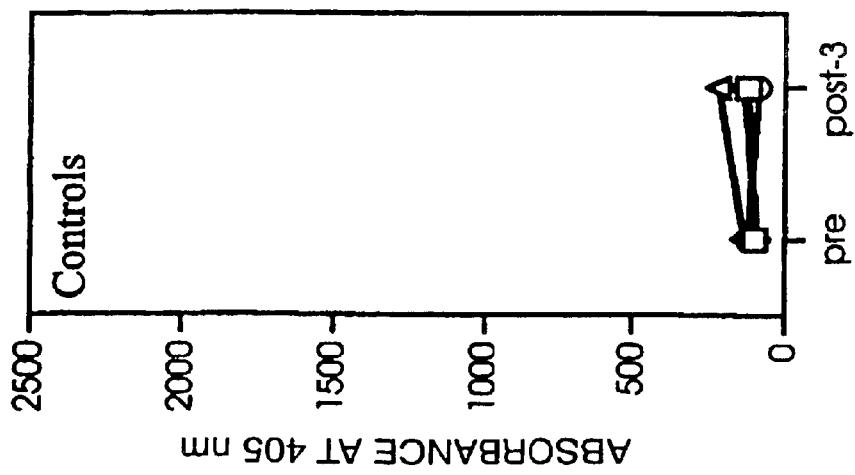

IMMUNIZATION AGAINST AND TREATMENT FOR INFECTION BY H. PYLORI

This application is related to United Kingdom patent applications GB 9809398.2 (filed 30th Apr. 1998) and GB 9820976.0 (filed 25th Sep. 1998), which applications are hereby incorporated in their entirety by reference.

TECHNICAL FIELD

The present invention relates to a method of protection against or treatment of an H. pylori infection, comprising non-mucosal administration of an effective amount of one or more H. pylori antigens.

BACKGROUND OF THE INVENTION

H. pylori was isolated in 1982 by B. Marshall and J. Warren using microaerophilic conditions that had been developed to grow Campylobacter jejuni. H. pylori bacteria are S-shaped, gram negative bacilli 2–3.5 μm in length and 0.5–1 μm in width (Blaser, M. J., and J. Parsonnet. 1994. J. Clin. Invest. 94:4–8). It is now (only recently) known that infection with H. pylori is the most common infection in the world. In developing countries 80% of the population is infected by the bacterium at the age of 20, while in developed countries H. pylori infection increases with age from <20% in 30-year old people to >50% in 60-year olds (Axon, A T. 1995. Pharmacol. Ther. 9:585–588; Blaser and Parsonnet, 1994). The infection is transmitted by either the oro-fecal or the oro-oral route (Blaser and Parsonnet, 1994). Infection occurs during the first years of life and persists forever. Once established, the infection is chronic, possibly permanent. Risk factors for infection are crowding, poor hygiene and host-specific genetic factors.

The complete genome sequence of H. pylori has been published (Tomb, J.-F., et al. 1997. Nature 388:539–547). A brief review of this article and a general review of the biology of H. pylori can be found in Doolittle, R. F. 1997. Nature 388:515–516.

Chronic infection of the human gastroduodenal mucosac by H. pylori is frequently associated with chronic gastritis, peptic ulcer, and increases the risk of occurrence of gastric malignancies such as adenocarcinoma and low grade B cell lymphoma (Blaser and Parsonnet, 1994; Parsonnet, J., et al. 1991. N. Engl. J. Med. 325: 1127–1231; Parsonnet, J., et al. 1994. N. Engl. J. Med. 330: 1267–1271). Most of the infections remain asymptomatic, whereas symptomatic, severe diseases correlate epidemiologically with the infection by a subset of H. pylori strains, called Type I (Blaser, M. J., et al. 1995. Cancer Res. 55:2111–2115; Covacci, A., et al. 1997. Trends Microbiol. 5:205–208; Covacci, A., et al. Proc. Natl. Acad. Sci. U.S.A. 90:5791–5795; Eck, M., et al. 1997. Gastroenterology. 112:1482–1486; Xiang, Z., et al. 1995. Infect. Immun. 63:94–98). This subset of strains is endowed with increased virulence due to the expression of a biologically active toxin (VacA), which is cytopathic to gastric epithelial cells in vitro and in vivo (Ghiara, P., et al. 1995. Infect. Immun. 63:4154–4160; Harris, P. R., et al. 1996. Infect. Immun. 64:4867–4871; Telford, J. L., et al. 1994. J. Exp. Med. 179:1653–1658), and also to the acquisition of a pathogenicity island (PAI), called cag, which contains a set of genes encoding several virulence factors (Censini, S., et al 1996. Proc. Natl. Acad. Sci. USA. 93:14648–14653) which are responsible for the induction of the synthesis of the neutrophil chemotactic cytokine IL-8 by the gastric epithelial cells (Censini et al, 1996).

H. pylori factors that have been identified so far include the flagella that are probably necessary to move across the mucus layer, see for example, Leying et al. 1992. Mol. Microbiol. 6:2863–2874; the urease that is necessary to neutralize the acid environment of the stomach and to allow initial colonization, see, for example, Cussac et al. 1992. J. Bacteriol. 174:2466–2473, Perez-Perez et al. 1992. J. Infect. Immun. 60:3658–3663, Austin, et al. 1992. J. Bacteriol. 174:7470–7473, WO 90/04030; the H. pylori cytotoxin (sometimes referred to as VacA, as it causes vacuolation), see, for example, WO 93/18150, Telford, J. L. et al. 1994. J. Exp. Med. 179:1653–1658, Cover et al. 1992. J. Bio. Chem. 267:10570–10575, Cover et al. 1992. J. Clin. Invest. 90:913–918, Leunk, 1991. Rev. Infect. Dis. 13:5686–5689; the H. pylori heat shock proteins (hsp), see, for example, WO 93/18150, Evans et al. 1992. Infect. Immun. 60:2125–2127, Dunn et al. 1992. Infect. Immun. 60:1946–1951, Austin et al., 1992; and the cytotoxin-associated protein, CagA, see, for example, WO 93/18150, Covacci, A., et al. 1993. Proc. Natl. Acad. Sci. USA 90:5791–5795, Tummuru, M. K., et al. 1994. Infect. Immun. 61:1799–1809.

Currently, H. pylori strains can be partitioned into at least two major groups, which either express (Type I) or do not express (Type II) the cytotoxin (VacA) and the CagA proteins. Type I strains contain the CagA and toxin genes and produce active forms of these antigens. Type II strains lack the CagA locus and fail to express the cytotoxin. The association between the presence of the CagA gene and cytotoxicity suggests that the production of the CagA gene is necessary for the transcription, folding, export or function of the cytotoxin. Epidemiological analysis indicate that Type I bacteria are associated with duodenal ulcerations, gastric ulceration and severe forms of active gastritis.

For a general review of the pathogenic role of H. pylori in peptic ulcer, see Telford, J. L., et al. 1994. TIBTECH 12:420–426.

H. pylori culture supernatants have been shown by different authors to contain an antigen with a molecular weight of 120, 128 or 130 kDa (Apel, et al. 1988. Zentralblat für Bakteriol. Microb. Und Hygiene 268:271–276; Crabtree, et al. 1992. J. Clin. Pathol. 45:733–734; Cover, et al. 1990. Infect. Immun. 58:603–610; Figura, et al. 1990. H. pylori, gastritis and peptic ulcer (eds. Malfrtheiner, et al.), Springer Verlag, Berlin). Whether the difference in size of the antigen described was due to interlaboratory differences in estimating the molecular weight of the same protein, to the size variability of the same antigen, or to actual different proteins was not clear. This protein is very immunogenic in infected humans because specific antibodies are detected in sera of virtually all patients infected with H. pylori (Gerstenecker, et al. 1992. Eur. J. Clin. Microbiol. 11:595–601).

A protein known as NAP (neutrophil activating protein— Evans D. J., et al. 1995. Gene 153:123–127; WO 96/01272 & WO 96/01273, especially SEQ ID NO:6; see also WO 97/25429), which is found in both type I and II strains, appears to be protective when tested in the H. pylori mouse model (Marchetti, M., et al. 1995. Science. 267:1655–1658). NAP is a homodecamer of 15 kDa subunits, and it has been proposed that the multimeric complex has a ring-shaped structure which spontaneously forms hexagonal paracrystalline structures. The assembled protein appears to interact with glycosphingolipid receptors of human neutrophils.

A number of other H. pylori antigens are described in WO 98/04702, including ureaseB (SEQ ID NO: 4), HopX (SEQ ID NO: 21), HopY (SEQ ID NO: 21), 36 kDa (SEQ ID NO:

26), 42 kDa (SEQ ID NO: 25), and 17 kDa (SEQ ID NO: 27). Urease is also described in, for example, EP-B-0367644 (protein with urease activity), EP-A-0610322 (ureaseE, F, G, H and I), EP-A0625053 (urease protein) and EP-A-0831892 (multimeric forms of urease). Other *H. pylori* antigens include the 54 kDa (SEQ ID NO: 2) and 50 kDa (SEQ ID NO: 1) proteins described in EP-A-0793676.

Discussions of various virulence factors of *H. pylori* can be found in, for example, EP-A-93905285.8 and EP-A-96908300.5.

Colonization of the mucosa of the stomach by *H. pylori* is today recognized as the major cause of acute and chronic gastroduodenal pathologies in humans (Blaser and Parsonnet, 1994; Covacci et al, 1997). The recognition of the infectious nature of the illness is having a major impact in the treatment of the disease that is shifting from the treatment of symptoms by anti-H2 blockers to the eradication of the bacterial infection by antibiotic regimen.

In spite of the unquestionable successes that will be achieved with antibiotic treatment, it should be remembered that such treatment inevitably leads to the occurrence of resistant strains that in the long term will make antibiotics ineffective. This suggests that vaccination, which classically is the most effective way to prevent and control infectious diseases in a large population, could be used to prevent infection and possibly also to treat the disease.

The increasing importance of *H. pylori* in the induction of a wide variety of gastric pathologies has represented a major challenge for the development of efficacious prophylactic and/or therapeutic strategies. To better understand the interactions between the bacterium and the host, much effort has focused on the development of appropriate animal models of infection reproducing aspects of the natural human infection.

Several animal models of infection and disease have been developed aiming at studying the pathogenesis of infection and development of preventive and therapeutic strategies. Many of these models are highly impractical, since they employ monkeys (Dubois, A., et al. 1994. Gastroenterology. 10:1405–1417) or species that are kept under gnotobiotic (that is, germ-free) conditions, for example germ-free dogs or piglets (Krakowka, S., et al. 1987. Infect. Immun. 55: 2789–2796; Radin, M. J., et al. 1990. Infect. Immun. 58: 2606–2612). Colonization of gnotobiotic piglets (Krakowka et al, 1987) has been reported using *H. pylori* strains isolated from patients with gastroduodenal diseases. However piglets cannot be kept under germ-free conditions for more than 2 months (Radin et al., 1990) mainly due to their nutritional needs.

Successful infection of specific pathogen-free (SPF) cats has been described using a strain isolated from conventional cats (Fox, J. G., et al. 1995. Infection and Immunity. 63: 2674–2681; Handt, L. K., et al. 1995. J. Clin. Microbiol. 33:2280–2289). Gnotobiotic beagle pups have also been infected with a human *H. pylori* isolate and kept under germ-free conditions for 30 days. However, in this model no data are available on long term infections with *H. pylori* (Radin et al., 1990). Other experimental animal models include athymic nu/nu or germ-free mice (Karita, M., et al. 1991. Am. J. Gastroenterol. 86:1596–1603).

The major drawbacks of these experimental infections, however, are the sophisticated and expensive housing systems required, and, more importantly, the peculiar immunological status of the gnotobiotic or immunodeficient hosts employed. More recently, *H. pylori*, freshly isolated from human gastroduodenal biopsies, have been adapted to persistently colonize the gastric mucosa of xenobiotic mice (Marchetti et al., 1995). This model has proven particularly useful to assess the feasibility of either preventive (Manetti, R., et al. 1997. Infect. Immun. 65:4615–4619; Marchetti et al., 1995; Marchetti, M., et al. 1998. Vaccine 16: 33–37; Radcliff, F. J., et al. 1997. Infect. Immun. 65:4668–4674) or therapeutic (Ghiara, P., et al. 1997. Infect. Immun. 65:4996–5002) vaccination, as well as for the in vivo screening of anti-*H. pylori* antimicrobials (Lee, A., et al. 1997. Gastroenterol. 112:1386–1397), and for studying the pathogenesis of infection (Sakagami, T., et al. 1996. Gut. 39:639–648). However, to evaluate gastric infection, mice have to be sacrificed; the pathological changes induced by the chronic infection and/or the effect of therapeutic or immunizing regimens cannot, therefore, be followed up in the same individual animal.

In United Kingdom patent application GB 9801000.2 (filed 16th Jan. 1998) and associated International patent application PCT/IB99/00217 (filed 15th Jan. 1999), there is described for the first time an animal model which can reproduce symptoms which have been clearly associated with the acute phases of infection with *H. pylori* in humans (Marshall, B. J., et al. 1985. Med. J. Australia. 142:436–439; Mitchell, J. D., et al. 1992. Am. J. Gastroenterol. 87:382–386; Morris, A., and G. Nicholson. 1987. Am. J. Gastroenterol. 82:192–199; Sobala, G. M., et al. 1991, Gut 32:1415–1418). The invention described in GB 9801000.2 and PCT/IB99/00217 is based on the discovery that *H. pylori* can persistently colonize the gastric mucosa of conventional xenobiotic dogs, and that this colonization causes acute symptoms, histopathological lesions and elicits specific immune responses. Thus, the animal model provided in GB 9801000.2 and PCT/IB99/00217 is ideal for studying the efficacy of treatments for *H. pylori* infection.

As *H. pylori* is a mucosa-related infection, where the bacteria do not invade the surrounding host cells, attempts to develop vaccines or treatments against the disease have concentrated on mucosal administration, specifically oral administration into the gastro-intestinal tract. Thus, as it had previously been thought that local (mucosal) treatment at the site of the *H. pylori* infection was necessary, the thrust of research in this area has been to develop mucosa-associated anti-*H. pylori* antibodies by the mucosal administration of prophylactics/therapeutics (see, for example: Chen, M., et al. 1992. Lancet 339:1120–1121; Ferrero, R. L., et al. 1994. Infect. Immun. 62:4981–4989; Michetti, P., et al. 1994. Gastroenterology 107:1002–1011; Lee, A., et al. 1994. Infect. Immun. 62:3594–3597; Doidge, C., et al. 1994. Lancet 343:974–979; Marchetti et al., 1995; Lee, C. K., et al. 1995. J. Infect. Dis. 172:161–172; Corthesy-Theulaz, I., et al. 1995. Gastroenterology 109:115–121; Cuenca, R., et al. 1996. Gastroenterology 110:1770–1775; Radcliff, F. J., et al. 1996. Vaccine 14:780–784; Stadtlander, C. T. K. H., et al. 1996. Dig. Dis. Sci. 41:1853–1862; Ferrero, R. L., et al. 1997. Gastroenterology 113:185–194; Weltzin, R., et al. 1997. Vaccine 15:370–376; Radcliff et al., 1997; Ghiara et al., 1997; Marchetti et al., 1998).

However, it has been shown in the present invention that a systemic protective effect against challenge with infectious *H. pylori* can be unexpectedly achieved using a non-mucosally administrated *H. pylori* antigen-containing composition. Specifically, it has been shown that, for instance, intramuscular (i.m.) immunization with whole *H. pylori* cell lysate can protect dogs against challenge with infectious *H. pylori*, and that the i.m. route, as an example of a non-mucosal route, can, unexpectedly, be considered for vaccination against this bacterium. Such a method may also be useful therapeutically in treating an already established *H. pylori* infection.

All documents (including patents, patent applications, research articles and books) which are mentioned in this application are hereby incorporated in their entirety by reference.

SUMMARY OF THE INVENTION

The present application is therefore based on the discovery that *H. pylori* antigen-containing compositions against *H. pylori* can be administered non-muscosally and still result in effective (systemic) protection from disease, despite the fact that the *H. pylori* bacteria are associated with the mucosa.

According to the present invention there is provided a method of protection against or treatment for infection by *H. pylori* comprising non-mucosal administration of an effective amount of one or more *H. pylori* antigens.

The term "comprising" means "including" as well as "consisting of".

Preferably, administration is parenteral, more preferably, intramuscular.

The one or more antigens administered may separately or in combination elicit a protective immune response in an animal, preferably, a mammal, more preferably a human.

At least one of the antigens may be a virulence factor of *H. pylori*. Examples of such virulence factors include VacA, CagA, NAP or urease. Other preferred antigens include HopX, HopY, 36 kDa, 42 kDa, and 17 kDa (see WO 98/04702) or 50 kDa antigen (see EP-A-0793676). The virulence factors of *H. pylori* administered preferably include VacA, CagA, NAP and urease. More preferably, the virulence factors include VacA, CagA and NAP. Most preferably, the virulence factors include CagA and NAP.

The *H. pylori* antigens administered may consist of only virulence factors or of only specific combinations of virulence factors such as VacA, CagA, NAP and urease; VacA, CagA and NAP; or CagA and NAP.

The antigens administered may also include non-*H. pylori* antigens.

The one or more antigens is/are preferably purified antigen(s) or a whole cell immunogen. The term "purified" means that at least one step of purification has been carried out such that a purified antigen is more pure than the same antigen in its natural context. There may, however, be present some impurities associated with such purified antigens. The term "purified" includes the situation where an antigen is "isolated". In this case, the antigen is generally not associated with any other substance which may adversely affect its ability to protect against or treat infection by *H. pylori*. Thus, the term "isolated" implies the highest degree of purification.

The antigens are obtained by various usual methods, i.e. by purification/isolation from cell culture, recombinant technology or by chemical synthesis. The whole cell immunogen is preferably prepared by extraction from *H. pylori* cells. The extraction may be carried out by lysis or sonication of the *H. pylori* cells or any other suitable method. The whole cell immunogen may be or may comprise inactivated *H. pylori* cells.

An adjuvant is preferably co-administered with the one or more *H. pylori* antigens. Preferably the adjuvant is aluminium hydroxide or MF59™ (see WO 90/14837; EP-B-0399843; Ott et al. Chapter 10 of *Vaccine Design: The subunit and adjuvant approach,* eds. Powell & Newman, Plenum Press 1995)

The one or more antigens may also be in association with one or more pharmaceutically acceptable excipients.

The present invention also provides the use of an effective amount of one or more *H. pylori* antigens in the manufacture of a medicament for non-mucosal administration for protection against or treatment for infection by *H. pylori*.

The present invention further provides a pharmaceutical composition for non-mucosal administration comprising one or more *H. pylori* antigens and one or more pharmaceutically acceptable excipients. This is preferably an immunogenic composition.

The one or more antigens of the pharmaceutical composition may separately or in combination elicit a protective immune response in an animal, preferably a mammal, more preferably, a human.

Preferably, at least one of the antigens is a virulence factor of *H. pylori*. Examples of such virulence factors are given above, along with examples of other preferred antigens.

The pharmaceutical composition preferably includes at least the virulence factors of VacA, CagA, NAP and urease. More preferably, the pharmaceutical composition includes at least the virulence factors of VacA, CagA and NAP. Most preferably, the pharmaceutical composition includes at least the virulence factors of CagA and NAP.

The *H. pylori* antigens of the pharmaceutical composition may consist of only virulence factors or of only specific combinations of virulence factors such as VacA, Cag NAP and urease, VacA, CagA and NAP, or CagA and NAP.

The antigens of the pharmaceutical composition may also include non-*H. pylori* antigens.

The one or more antigens is/are preferably purified antigen(s) or a whole cell immunogen as described above.

The pharmaceutical composition may also further comprise an adjuvant. Preferably, the adjuvant is aluminium hydroxide or MF59™.

The pharmaceutical composition of the invention can be an immunogenic composition such as, but not limited to, a vaccine.

The present invention therefore also provides an immunogenic composition for non-mucosal administration comprising one or more *H. pylori* antigens and one or more pharmaceutically acceptable excipients.

Immunogenic compositions and vaccines according to the invention may either be prophylactic (i.e. to prevent infection) or therapeutic (i.e. to treat disease after infection). Such vaccines comprise antigen or antigens, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a bacterial toxoid.

Preferred adjuvants to enhance effectiveness of the composition include, but are not limited to: (1) aluminium salts (alum), such as aluminum hydroxide, aluminium phosphate, aluminium sulphate, etc.; (2) oil-in-water emulsion formulations (with or without other specific immunostimulating agents such as muramyl peptides or bacterial cell wall components), such as for example (a) MF59™, containing 5% Squalene, 0.5% Tween™ 80, and 0.5% Span 85 (optionally containing various amounts of MTP-PE, although not required) formulated into submicron particles using a microfluidizer (b) SAF, containing 10% Squalene, 0.4% Tween 80, 5% pluronic-blocked polymer L121, and thr-MDP either microfluidized into a submicron emulsion or vortexed to generate a larger particle size emulsion, and (c) Ribi™ adjuvant system (RAS), containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ may be used or particles generated therefrom such as ISCOMs (immunostimulating complexes); (4) Freund's complete and incomplete adjuvants (CFA & IFA); (5) cytokines, such as interleukins (e.g. IL-1, IL-2, IL4, IL-5, IL6, IL-7, IL-12, etc.), interferons (e.g. IFNγ), macrophage colony stimulating factor (M-CSF), tumor necrosis factor (TNF), etc.; and (6) other substances that act as immunostimulating agents to enhance the efficacy of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-huydroxyphosphoryloxy)-ethylamine (MTP-PE), etc.

The immunogenic compositions (eg. the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvanticity effect, as discussed above.

Immunogenic compositions used as vaccines comprise an immunologically effective amount of the antigenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are administered non-mucosally, more specifically parenterally eg. by injection, either subcutaneously or intramuscularly. Transdermal or transcutaneous administration may also be used. Dosage treatment may be a single dose schedule or a multiple dose schedule. The vaccine may be administered in conjunction with other immunoregulatory agents.

According to the present invention, there is further provided the use of the pharmaceutical composition as described above or the immunogenic composition as described above for protection against or treatment for infection by *H. pylori*.

BRIEF DESCRIPTION OF THE DRAWINGS

FIG. 4 shows the schedule of the experiment to determine whether Beagle dogs may be protected against a challenge with *H. pylori* using purified antigens given i.m.

DETAILED DESCRIPTION OF THE INVENTION

Whole cell *H. pylori* vaccine

Figure 1A:
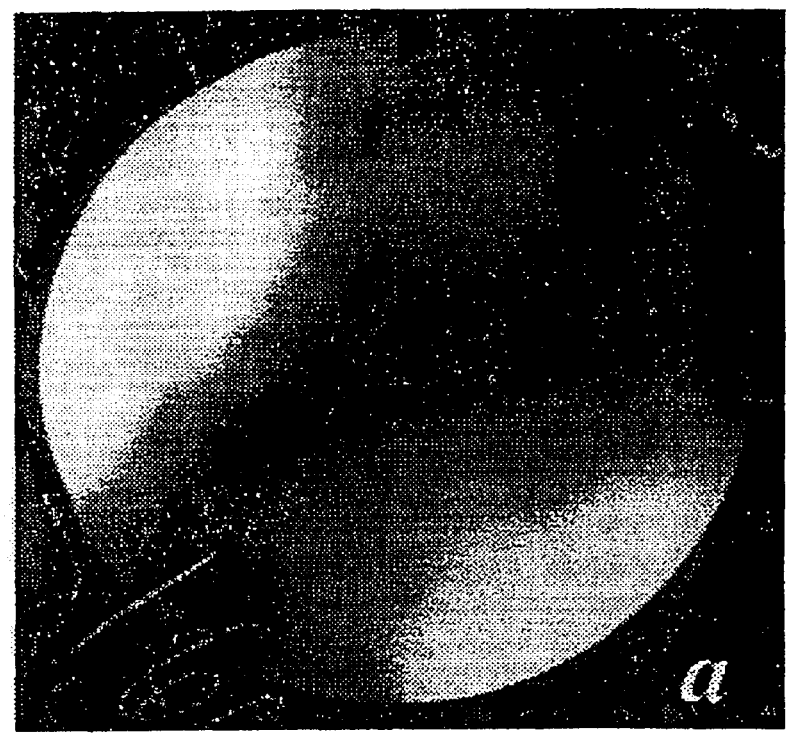
FIG. 1 shows endoscopic examination of the antral region of protected dogs (FIG. 1A) and control (infected) dogs (FIG. 1B) 42 days after challenge with *H. pylori*.

As an embodiment of the invention, the feasibility of immunizing conventional dogs with whole cell *H. pylori* vaccine (i.e. *H. pylori* cell lysate) was investigated. It is shown that such a preparation can elicit an immunity that provides a protective effect against a later challenge with infectious *H. pylori*.

Immunogenicity

The protective effect of a whole cell *H. pylori* vaccine was investigated in dogs challenged with infectious *H. pylori*. The details of the experimental procedures followed are set out later. As compared to time 0 and to control dogs, i.m. immunization induced very high titers of serum IgG antibodies as shown in Table 1. I.m. immunization with *H. pylori* lysate also induced production of antigen-specific serum IgA antibodies.

Symptoms

Control dogs #2 and #3 had diarrhoea during the first week after the last challenge. Control dog #2 also had vomiting. There were no symptoms of *H. pylori* infection in the i.m. group.

Urease Test on Gastric (antral) Biopsy and on Gastric Lavage

This assay, performed on antral biopsies and gastric lavage taken 10 days after the last challenge, was positive in the control group, and negative in the i.m.group as shown in Table 2 below, even 24 h later. These data were also confirmed at day 42 post-challenge.

Conclusions

Taken together these data show that i.m. immunization with *H. pylori* lysate can protect dogs against challenge with infectious *H. pylori*, and that the i.m. route can be considered for vaccination against this bacterium.

Purified *H. pylori* Antigen Vaccine

As a further embodiment of the invention, the feasibility of immunizing conventional dogs with purified *H. pylori* antigens was also investigated. It is shown that such a preparation can elicit an immunity that provides a protective effect against a later challenge with infectious *H. pylori*.

Immunogenicity

The protective effect of purified *H. pylori* antigens (specifically VacA, CagA and NAP) was investigated in dogs challenged with infectious *H. pylori*. The details of the

TABLE 1

Immunogenicity of the *H. pylori* lysate given four times Intramuscularly to Beagle dogs

| | | Serum IgG titers to: | | | | | | Serum IgA titers to |
| | | *H. pylori* lysate | | CagA | | NAP | | *H. pylori* lysate |
| Dog no. | Immunization route | Pre* | Post-4 | Pre | Post-4 | Pre | Post-4 | Pre | post-4 |
| --- | --- | --- | --- | --- | --- | --- | --- | --- | --- |
| 1 | nil (control) | <100§ | <100 | <100 | <100 | <100 | <100 | <20 | <20 |
| 2 | nil (control) | <100 | <100 | <100 | <100 | <100 | <100 | <20 | <20 |
| 3 | nil (control) | <100 | <100 | <100 | <100 | <100 | <100 | <20 | <20 |
| 4 | Intramuscular | <100 | ≧25000 | <100 | 12800 | <100 | ≧12800 | <20 | 1280 |
| 5 | Intramuscular | <100 | ≧25000 | <100 | 12800 | <100 | ≧12800 | <20 | 320 |
| 6 | Intramuscular | <100 | ≧25000 | <100 | 6400 | <100 | ≧12800 | <20 | 640 |

*Pre: serum samples taken before the immunization; Post-4: serum sample taken after four immunizations, before the challenge.
§Titers are expressed as the last serum dilution giving an optical density equal or higher than 0.2. Titers <100 (IgG) and <20 (IgA) are considered as negative.

TABLE 2

| Group | dog # | biopsy | gastric lavage |
| --- | --- | --- | --- |
| Control | 1 | + | + |
| | 2 | + | + |
| | 3 | + | + |
| i.m. | 1 | − | − |
| | 2 | − | − |
| | 3 | − | − |

Endoscopy, Histology and Immunohistochemistry Results

Figure 1B:

Protected dogs showed normal mucosa at endoscopic examination at 42 days post-challenge (FIG. 1A), with a bright and smooth surface, without signs of hyperemia or edema. Conversely, in the control (infected) dogs, the gastric mucosa was heavily red and edematous, and had a rippled surface with appearance of plicae (FIG. 1B), suggestive of the nodular (follicular) gastritis observed previously and described in patent applications GB 9801000.2 and PCT/IB99/00217.

Figure 2A:
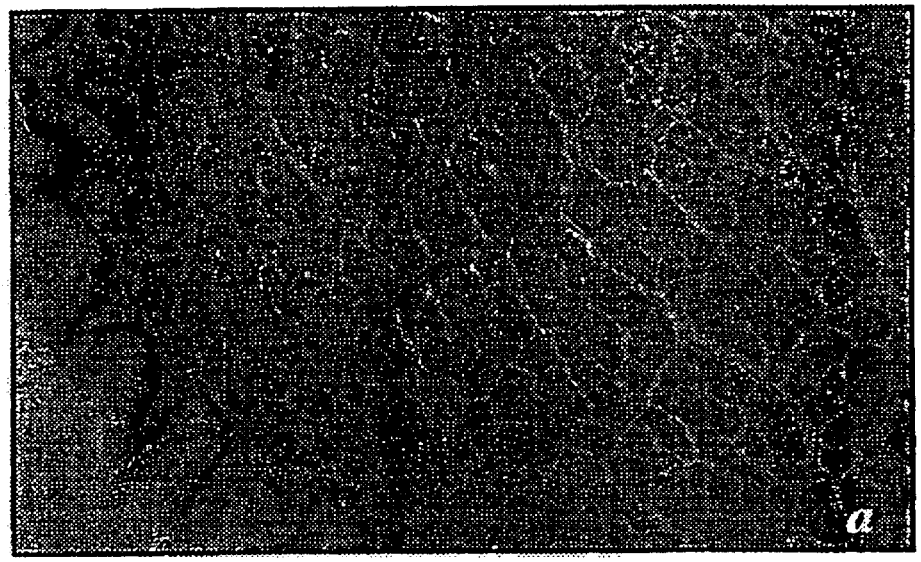
FIG. 2 shows histological examination (hematoxylin-eosin (HE) staining) of biopsies taken from the antral region of protected dogs (FIG. 2A, magnification=10×) and control (infected) dogs (FIG. 2B, magnification=10×.
FIG. 2C, magnification=40×.
FIG. 2D, magnification=100×) 42 days after challenge with *H. pylori*.
Figure 2B:
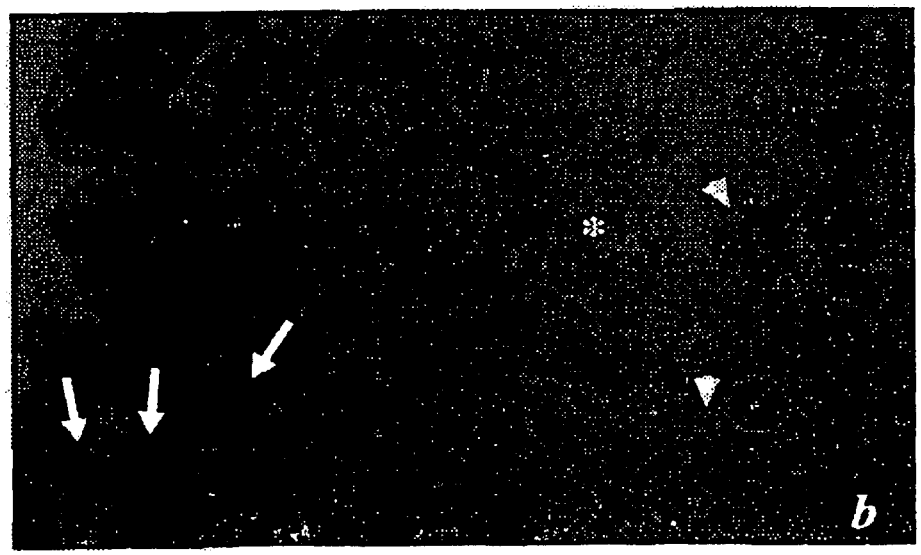
Figure 2C:
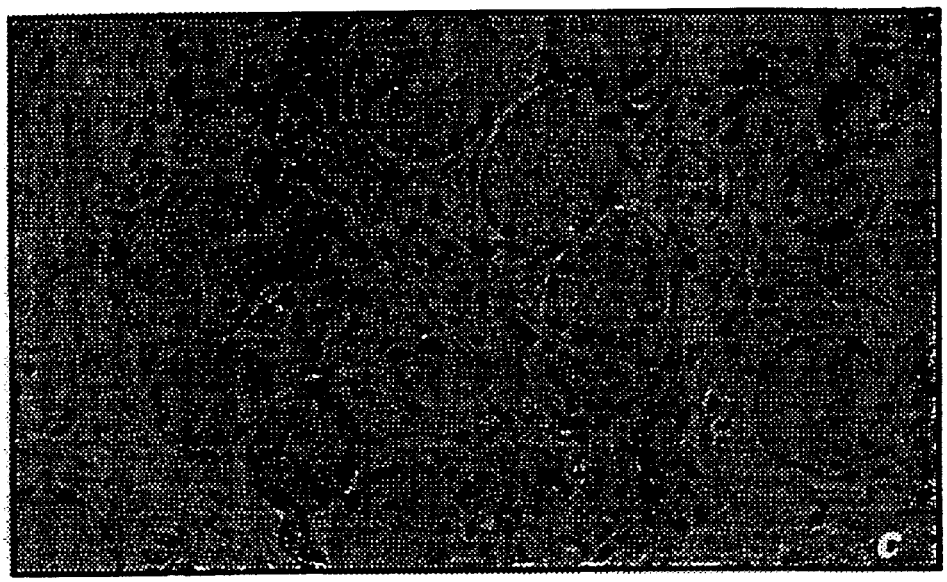
Figure 2D:
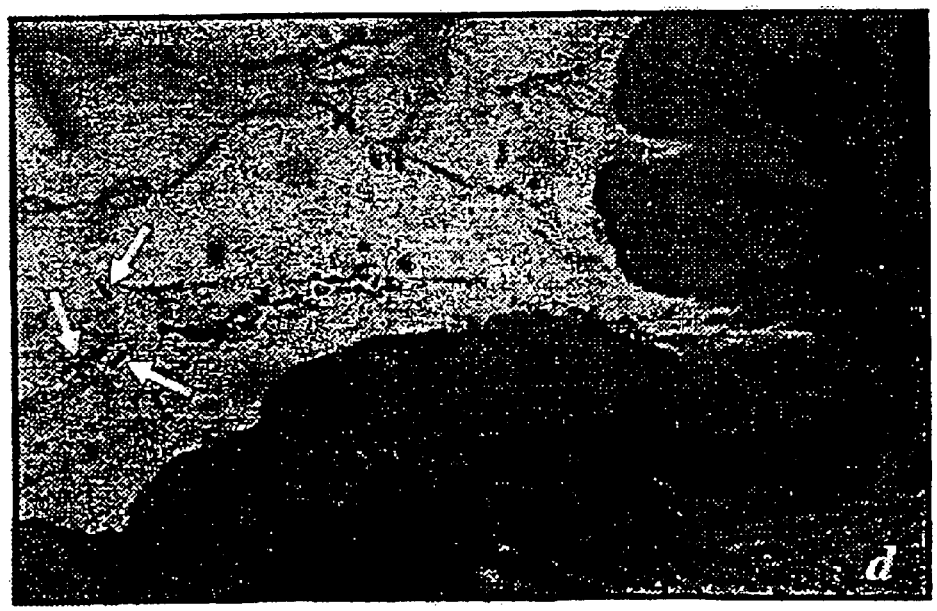

Histologically, the gastric mucosa of protected dogs conserved an intact structure, both at the surface and at the submucosa (FIG. 2A), whereas in infected dogs there was appearance of hyperemia (FIG. 2B, arrows), edema (FIG. 2B, asterisk), inflammatory cellular infiltrates (FIG. 2B, arrowheads and FIG. 2C): *H. pylori* was also easily identified in the mucous layer (FIG. 2D).

Figure 3A:
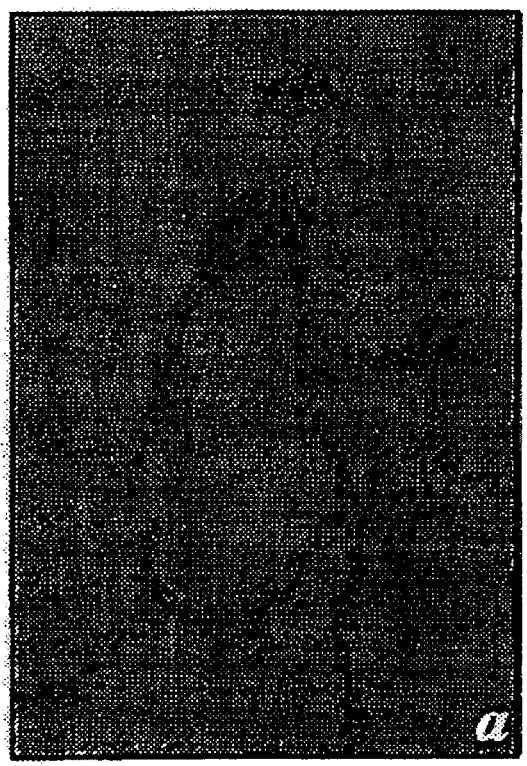
FIG. 3 shows immunohistochemical examination of biopsies taken from the antral region of protected dogs (FIG. 3A) and control (infected) dogs (FIG. 3B) 42 days after challenge with *H. pylori* (magnification=40×).
Figure 3B:
Figure 5B:
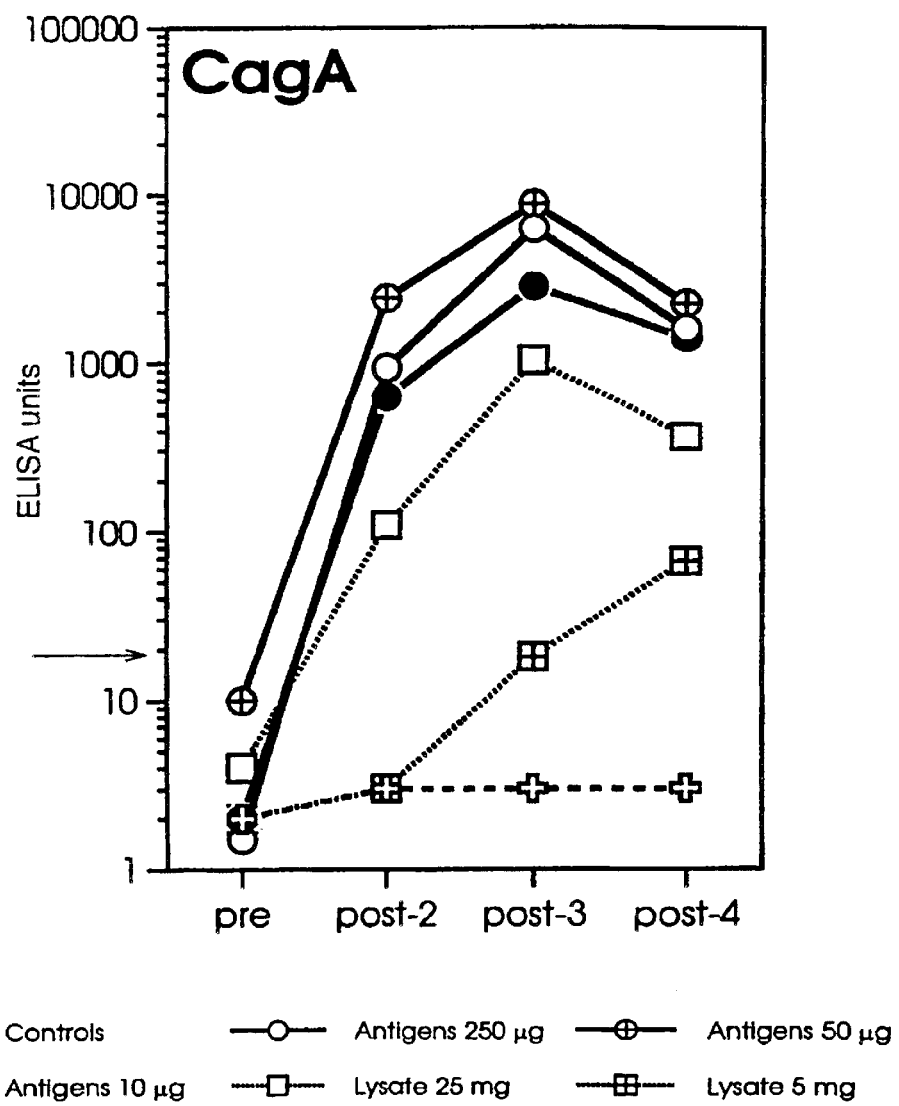
FIG. 5 shows serum antibody titers to recombinant VacA (FIG. 5A), to CagA (FIG. 5B) and to NAP (FIG. 5C) (averages) before the first immunization, and after the second, third and fourth immunizations i.m. with purified antigens or with whole cell lysate. The horizontal arrow individuates the lower limit for positive ELISA results.

All these data were confined by immunohistochemistry using an anti-VacA monoclonal antibody, which heavily stained epithelial cells of infected dogs (FIG. 3B, arrows), but not those of protected dogs (FIG. 3A).

experimental procedures followed are set out later. Immunization with these antigens induced very strong serum IgG antibody response specific for each antigen after only two doses. Titers increased after the third dose. Doses of 50 and 10 µg of antigens were as good as 250 µg to induce high titers of antigen-specific antibodies. Comparatively, lower antibody titers were detectable in dogs immunized with *H. pylori* lysate (see FIG. 5).

Figure 6A:
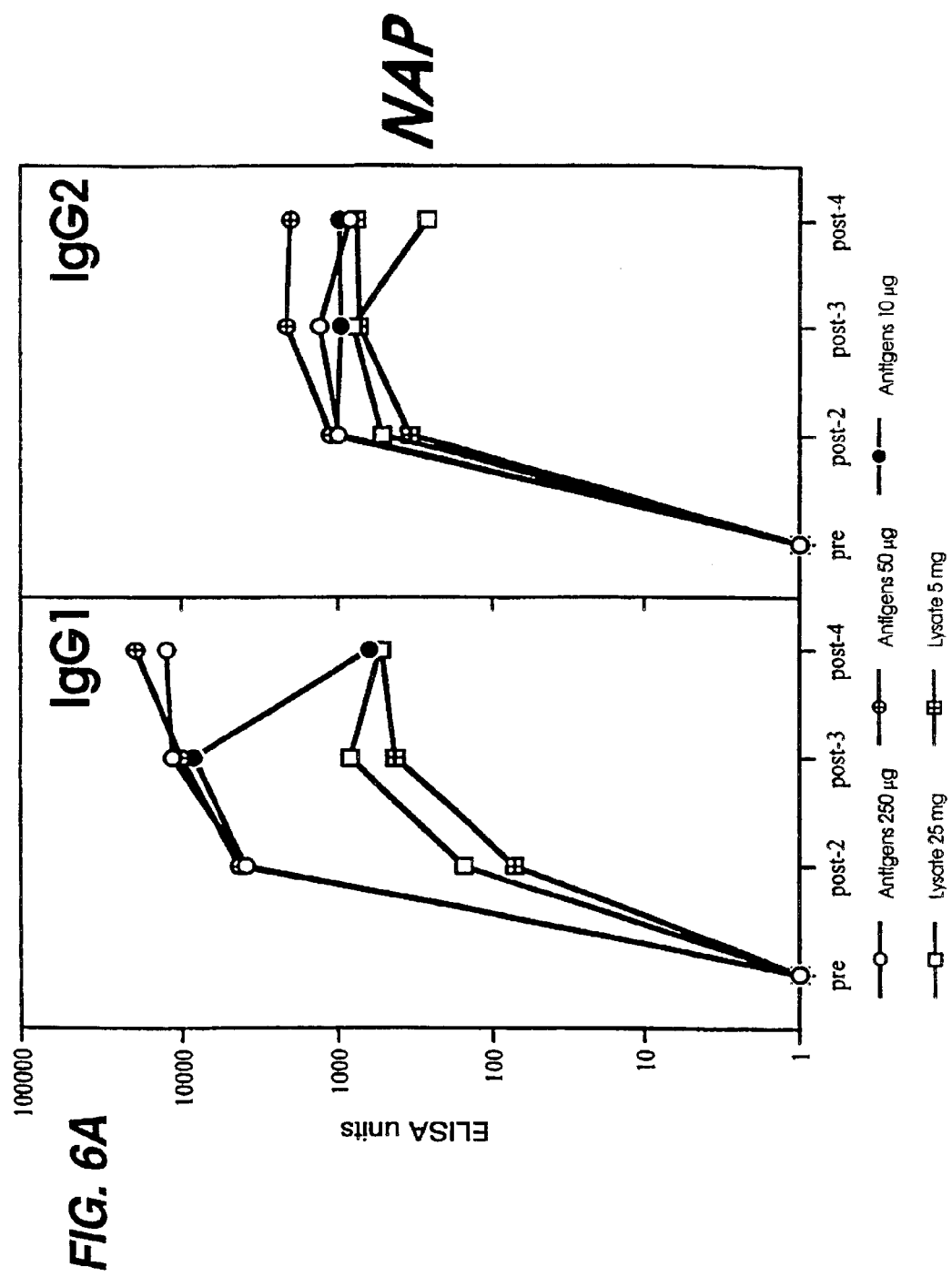
FIG. 6 shows the titers of serum IgG antibody subclasses IgG1 and IgG2 to CagA (FIG. 6A) and NAP (FIG. 6B) (average titers per groups immunized i.m. with purified antigens or with whole cell lysate) at the same time points as above (FIG. 5).
Figure 6B:
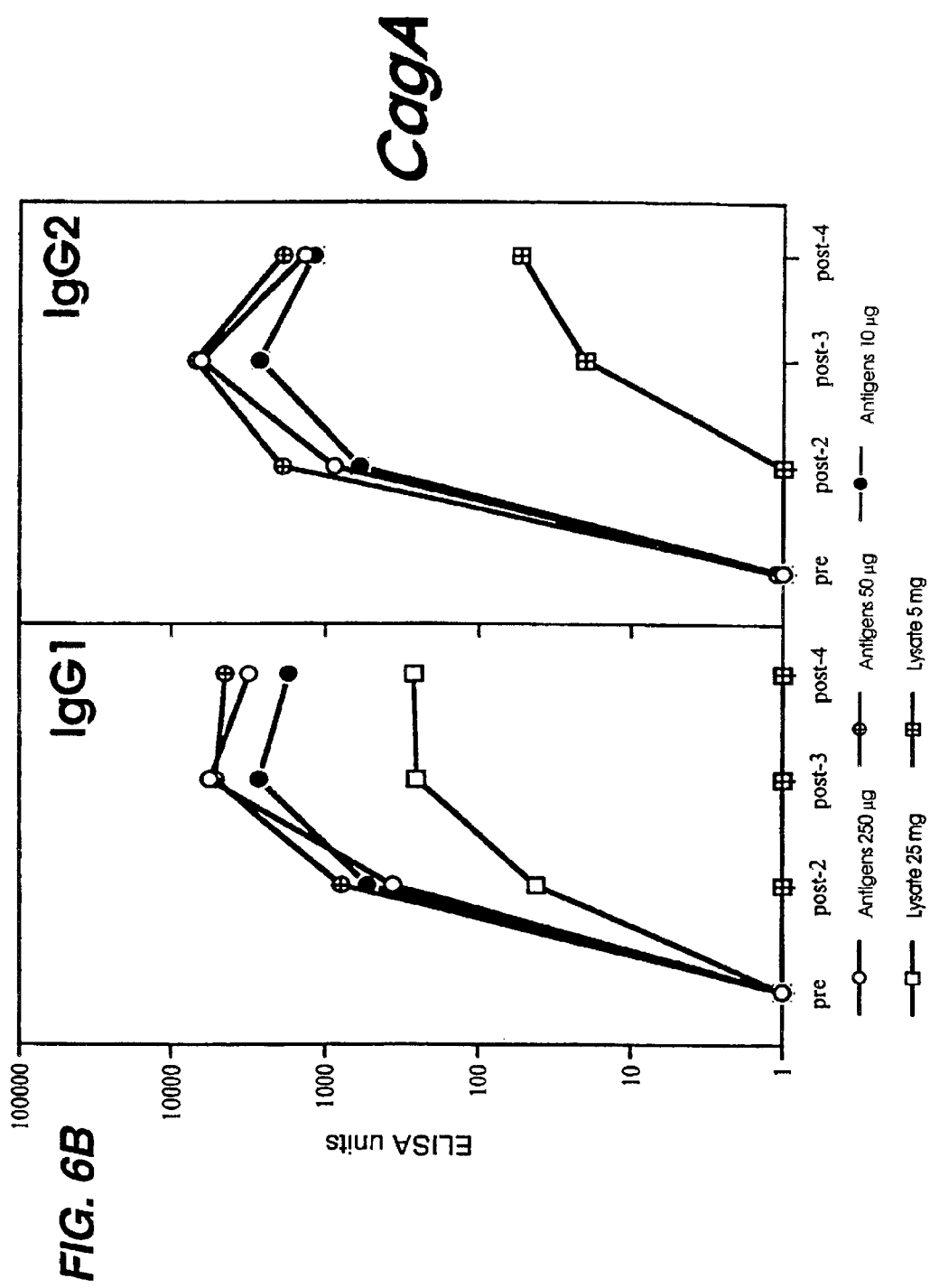

Immunization with these antigens also induced high titers of antigen-specific serum IgG1 and IgG2 antibodies, suggesting that this immunization induces both Th1- and Th2-type immune response, unlike what has already been observed in infected mice and dogs, in which a preponderant Th1-type immune response is evident (see FIG. 6).

Figure 7D:
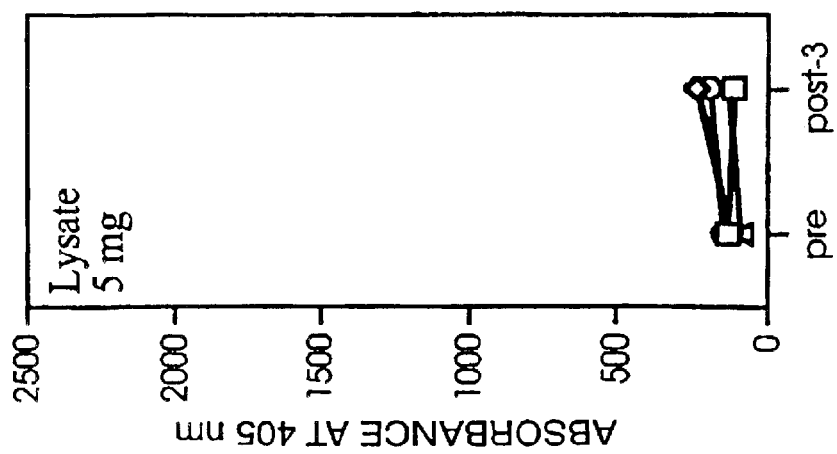
FIG. 7 shows serum IgA antibody titers to p95 (recombinant VacA) in Beagle dogs immunized i.m. with purified antigens (VacA, CagA and NAP) or with whole cell lysate (single dogs—FIGS. 7A to 7F) before immunization and after the third immunization. (Similar serum IgA antibody titers were observed against CagA.)
Figure 7E:
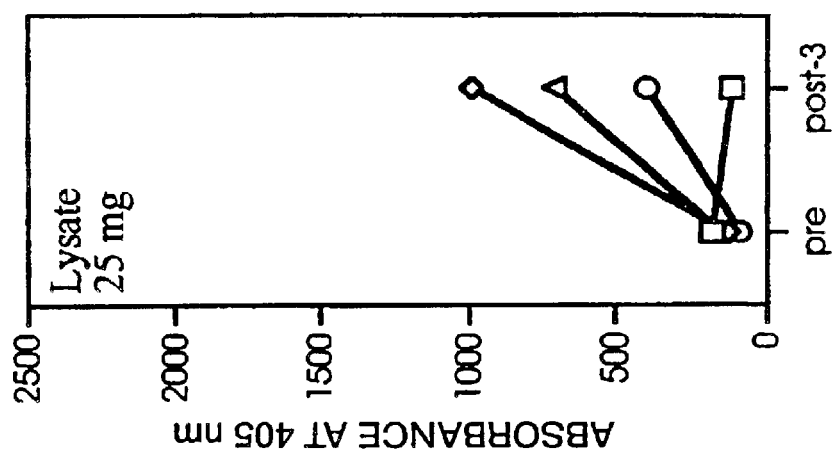
Figure 7F:
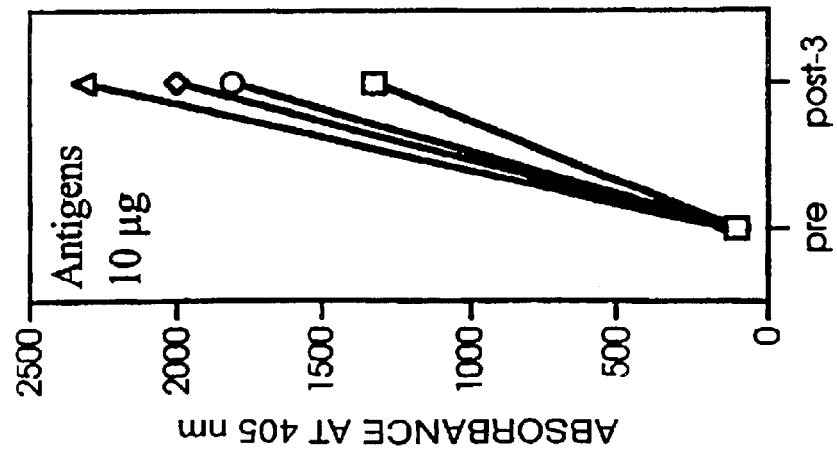

Dogs immunized in this manner also had detectable titers of antigen-specific IgA antibodies in the serum (see FIG. 7).

Endoscopy, Histology and Immunohistochemistry Results

Figure 8A:
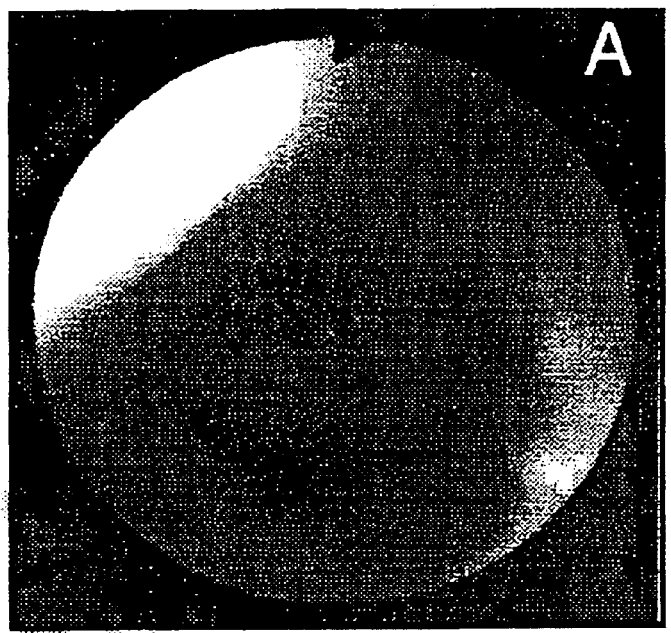
FIG. 8 shows the endoscopic image of protected (FIG. 8A) and non-protected (infected) (FIG. 8B) dogs taken about 8 weeks post-challenge.
Figure 8B:
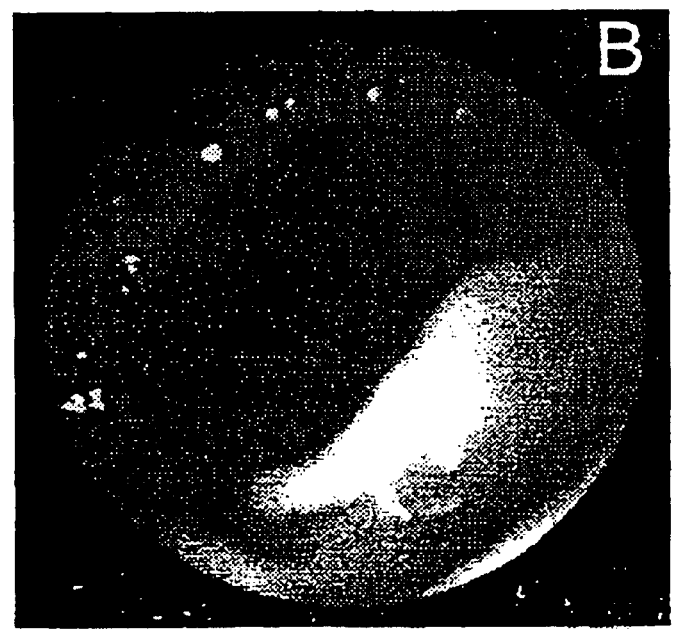
Figure 9B:
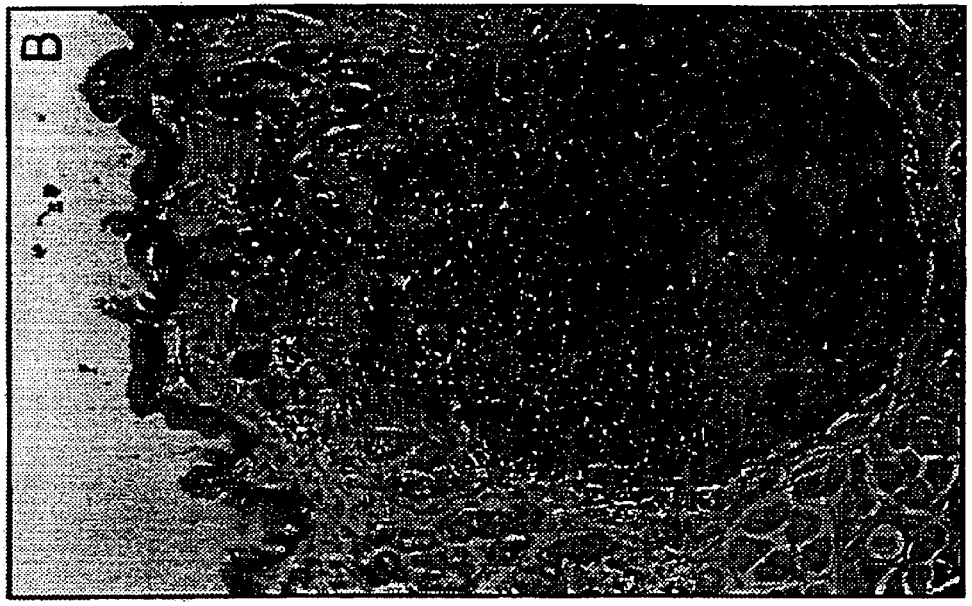
FIG. 9 shows the histology (HE staining, magnification=10×) of gastric mucosa from protected (FIG. 9A) and non-protected (infected) (FIG. 9B) dogs taken about 8 weeks post-challenge. Note in FIG. 9A the normal mucosa and submucosa. Conversely, in FIG. 9B, a large lymphoid follicle, disrupting the structure of the mucosa and the submucosa can be noted.
Figure 9A:
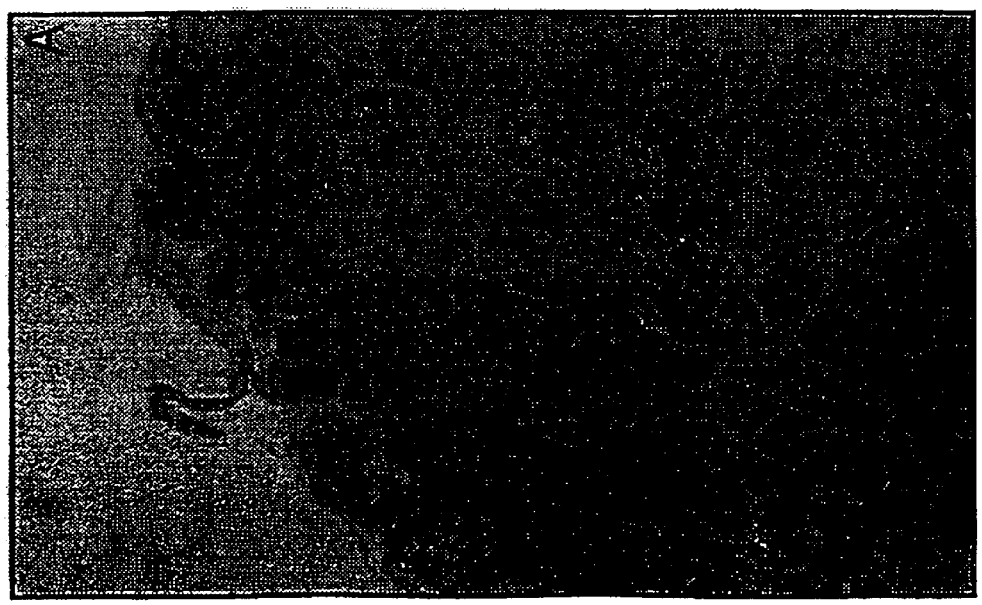
Figure 10A:
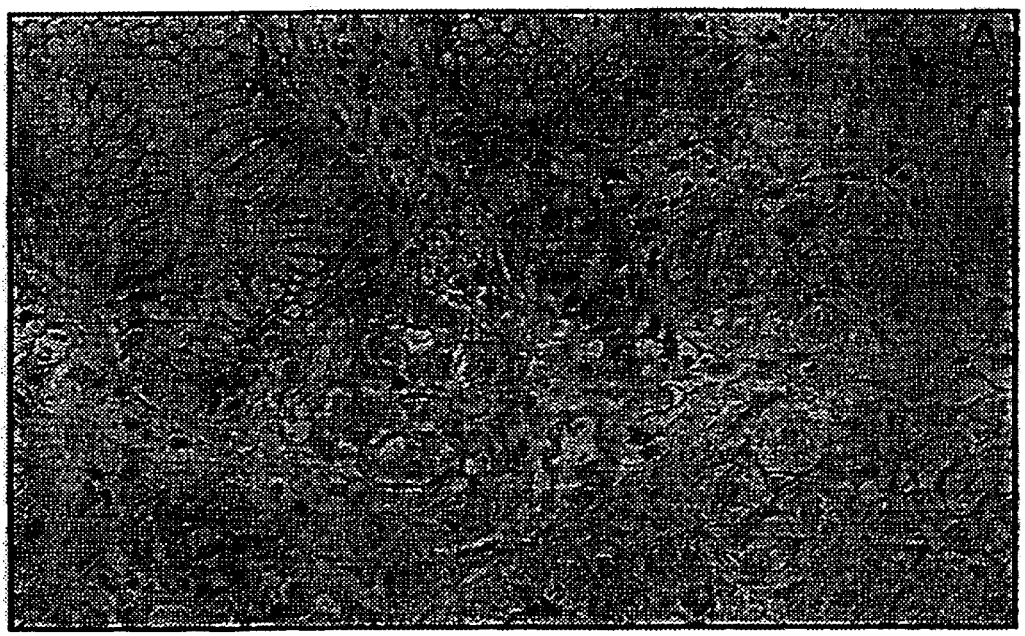
FIG. 10 shows the immunohistochemistry using anti-VacA monoclonal antibody taken about 8 weeks post-challenge (magnification=10×). Note the negative staining in protected dog (FIG. 10A) and the heavily positive staining in non-protected (infected) dog (FIG. 10B).
Figure 10B:

In protected animals (see Table 3—which gives the conclusive results on protection, based on all parameters taken together, including endoscopy (gastroscopy), histology and immunohistochemistry), gastric mucosa was normal at endoscopic investigation, at histology, and at immunohistochemistry (see FIGS. 8A, 9A and 10A, respectively). Non-protected (infected) animals showed hyperemic, heavily flogistic aspect of the gastric mucosa at endoscopy (FIG. 8B), with a diffuse infiltration with mononuclear cells aggregated in lymphoid follicle structures (FIG. 9B) disrupting the normal glandular structure. FIG. 10B shows a strong positivity at immunohistochemistry using an anti-VacA monoclonal antibody.

Conclusions

Taken together these data show that i.m. immunization with H. pylori antigens can protect dogs against challenge with infectious H. pylori.

TABLE 3

Intramuscular Immunization with purified antigens protects dogs against challenge with Helicobacter pylori

| Group | Dog # | Protection |
|---|---|---|
| Control | 1 | − |
|  | 2 | − |
|  | 3 | − |
|  | 4 | − |
| VacA/CagA/NAP 250 μg each | 5 | + |
|  | 6 | + |
|  | 7 | + |
|  | 8 | − |
| VacA/CagA/NAP 50 μg each | 9 | + |
|  | 10 | + |
|  | 11 | + |
|  | 12 | + |
| VacA/CagA/NAP 10 μg each | 13 | + |
|  | 14 | + |
|  | 15 | + |
|  | 16 | + |
| whole-cell lysate 25 mg | 17 | − |
|  | 18 | + |
|  | 19 | + |
|  | 20 | + |
| whole-cell lysate 5 mg | 21 | + |
|  | 22 | + |
|  | 23 | − |
|  | 24 | + |

Experimental

H. pylori Strains

SPM326s, a streptomycin-resistant derivative of the mouse-adapted H. pylori Type I (CagA+/VacA+) strain SPM326 (Marchetti et al., 1995), was grown as previously described (Marchetti et al., 1995) and used to challenge the dogs. The CCUG strain of H. pylori is well known in the art.

Animals

Six 4–6 months-old xenobiotic beagle dogs, all female (Morini s.a.s., S. Polo D'Enza, Italy), were selected on the basis of the absence of detectable serum IgG against Helicobacter spp. in Western blot (WB) analysis using total bacterial lysate as antigen (see below). The six dogs selected were housed in standard conditions and maintained on a diet of dry food (MIL, Morini s.a.s.) and tap water ad libitum. Upon arrival in our animal facilities, an additional WB analysis on sera confirmed their H. pylori status. The dogs were housed in individual cages and allowed to adapt for a month to the new environment. During the month of adaptation, two tests were carried out on fecal samples to assess the presence of intestinal parasites or common enteric pathogenic bacteria.

Preparation of H. pylori Lysate

Two pellets of H. pylori CCUG strain from two 5 liter fermenters (Olivieri, R. et al. 1993. J. Clin. Microbiol. 31:160–162) were obtained. After each pellet was resuspended in 50 ml of sonication buffer (50 mM $Na_2HPO_4 \cdot 2H_2O$, 300 mM NaCl, pH 7.8), the two resuspended pellets were mixed. The $OD_{530nm}$ of the combined resuspension was measured to determine bacterial concentration (=$3.2 \times 10^{10}$ CFU/ml). The resuspension was diluted with sonication buffer to bring the concentration to $2 \times 10^{10}$ CFU/ml. Before sonication, bacteria had the classical spiral form when viewed under the microscope. Sonication of the resuspended bacteria was then carried out on ice: 2 cycles of 4 minutes, and 2 cycles of 5 minutes, waiting one minute between each cycle. After sonication, all the bacteria appeared broken when viewed under the microscope. Protein concentration was then determined using the Bradford method (=57.5 mg/ml protein). Aliquots of the cell lysate were then prepared and frozen at −80° C. until use.

Immunization

Three dogs were immunized on day 0 intramuscularly (i.m.) with the prepared H. pylori lysate (the equivalent of $10^{10}$ CFU H. pylori (=28 mg/dose)) adsorbed onto 1 mg aluminium hydroxide (Chiron Behring GmbH & Co., Marburg, Germany; Lot No. 277345) in 1 ml volume. Immunizations were repeated on days 7, 14, and 22. Serum samples were taken on day 0, 21 (post-3) and 43 (post-4). The other three dogs, as a control group, were treated identically but saline was used in place of the H. pylori lysate.

Challenge with Infectious H. pylori

The dogs were then challenged on days 49, 51 and 53 with the mouse-adapted H. pylori SPM326s strain as follows: 24 h before each challenge the dogs were fasted. 2 h before bacteria inoculation, dogs received 10 mg/kg of cimetidine i.m. (Tagamet® 200; Smith Kline & French, USA). At the moment of challenge, the dogs were anesthetized with a mixture of 40 μg/kg of medetomidine chloridrate (Domitor®; Centralvet-Vetem s.p.a., Milano, Italy) and 5 mg/kg of ketamine (Ketavet®, Gellini, Latina, Italy) intravenously (i.v.); then a gastric lavage was performed with 100 ml of 0.2M $NaHCO_3$ sterile solution followed by oral challenge with 3 ml of a freshly prepared suspension of $10^9$ CFUs in sterile saline of the H. pylori strain SPM326s, grown under microaerobic conditions (see below), prepared immediately before the inoculation procedure. At the end of the bacterial inoculation, 200 μg/kg of the anesthetic antagonist atipamezole (Antisedan®; Centralvet-Vetem s.p.a., Milano, Italy) was administered and then dogs were again treated with cimetidine and fed after 2 h.

Post-challenge Follow-up

Ten and 42 days after the last challenge gastric endoscopies were performed using a 4.9-mm-diameter Pentax pediatric bronchoscope (Pentax Technologies, Zaventem, Belgium). At the same time, gastric biopsies were taken during the endoscopies using flexible pinch-biopsy forceps at the antrum, corpus fundus, and cardias for urease testing and for microbiological, histopathological and immunohistochemical analyses. Before each endoscopy the whole instrument and the flexible forceps were soaked in 4% glutaraldehyde for 45 minutes and then rinsed in sterile saline. To avoid cross-contamination among biopsies taken at different sites, the forceps were washed with tap water and lightly flame-sterilized before the collection of each bioptic sample. The above experimental protocol was approved by the Scientific and Ethical Commitee of the University of Pisa and received official authorization (DM No. 21/97-C) from the Italian Ministry of Health (Department of Veterinary Health, Food and Nutrition).

Rapid Urease Test

Antral biopsies and liquid from gastric lavage were incubated for up to 24 h in 1 ml of a 10% urea solution in distilled water added with two drops of a 1% phenol red solution (Sigma Chemical Co., St. Louis, Mo., USA) in sodium phosphate buffer, pH 6.5. A positive test is indicated by change of color (from orange to dark pink) in the medium; the time necessary for the color change is recorded. At time 0, endoscopy was carried out on the six dogs and antral biopsies were taken for the urease test. In all six dogs, the urease test was negative at time 0.

Histopathology and Transmission Electron Microscopy

Samples for histological, immunohistochemical and ultra-structural examination were taken from the biopsies at sites adjacent to those utilized for microbiological analysis. The samples were fixed in 10% buffered formalin and embedded in paraffin. 3 μm sections were stained with hematoxylin-eosin (H & E) and Alcian and Periodic acid Schiff's (PAS) staining using standard procedures for histopathological examination. Similar sections were also employed for immunohistochemical analyses using the Avidine-Biotine-Complex (ABC)-peroxidase technique with a monoclonal antibody (Mab) specific for *H. pylori* (Biogenesis Ltd, Poole, England, UK) or an anti-VarA mouse monoclonal antibody (C1G9) obtained by immunizing Balb/c mice with purified native *H. pylori* VacA (Burroni and Telford, unpublished observations). Biotinylated horse anti-mouse antibody was used as secondary antibody. The reaction was developed with 3-1-diaminobenzidine-chlorhydrate (DAB) (Sigma) for identification and location of bacterial antigen. For electron microscopic examination, other samples were fixed in Karnowsky, post-fixed in $OsO_4$, and embedded in Epon-Araldite (Polysciences Inc., Warrington, Pa., USA). Semi-thin sections were stained with toluidine blue for evaluation of cell damage, whereas ultra-thin sections were stained with uranyl acetate and lead citrate, and then examined with a Philips EM 301 transmission electron microscope (TEM) operating at 80 KV.

Detection of Anti-*H. pylori* Antibodies

SDS-PAGE of *H. pylori* (strain SPM326s) and WB analysis of sera were performed according to previously published procedures (Marchetti et al., 1995). Briefly, dog sera were diluted 1:200 and incubated for 2 h at room temperature. Then, horseradish peroxidase (HRP)-conjugated rabbit anti-dog IgG antibody (Nordic Immunological Laboratories, Tilburg, The Netherlands) was added at 1:2,000 dilution for 2 h, and the reaction was developed using 4-α-chloronaphtol as substrate. Detection of antibody against *H. pylori* by ELISA was carried out on 96-well plates coated overnight at 4° C. with the prepared CCUG strain lysate used for immunization (5 μg/well) or with purified native CagA or NAP (0.2 μg/well). Coated wells were blocked with PBS containing 5% non-fat milk. Twofold serial dilutions of the sera were incubated at 37° C. for 2 h and then washed with PBS. Antigen specific IgG titers were determined using a 1:4,000 dilution of HRP-conjugated goat anti-dog IgG antibody (Bethyl Laboratories, Inc., Montgomery, Tex., USA) for 2 h at 37° C. Antigen bound antibodies were revealed by adding o-phenylenediamine dihydrochloride (Sigma) as a substrate. Antibody titers were determined as previously described (Ghiara et al., 1997).

Intramuscular (i.m.) Immunization of Dogs with Purified *H. pylori* Antigens

VacA and CagA were expressed and purified as described in Ghiara, et al. 1997. NAP was expressed and purified as described in earlier patent applications GB 9807721.7 and PCT/IB99/00695. As shown in Table 4, groups of 4 dogs were immunized i.m. with:

(i) a mixture of recombinant VacA, CagA, and NAP (250, 50 or 10 μg of each antigen) adsorbed onto aluminium hydroxide (1 mg dose);

(ii) CCUG lysate (prepared as discussed above), at 25 or 5 mg per dose adsorbed onto aluminium hydroxide (1 mg dose);

(iii) aluminium hydroxide alone (1 mg dose).

Dogs were immunized 4 times at weekly intervals. Challenge with *H. pylori* was carried out 4 weeks later as already described. Samples (blood, biopsies, etc.—as previously described) were taken before immunization, after the second, third and fourth immunizations, and then 2–3 weeks and 8 weeks after the last challenge.

TABLE 4

IMMUNIZATION PROTOCOL
All antigens given intramuscularly with alum as adjuvant

| GROUP | DOGS | ROUTE | IMMUNOGEN | DOSE | ADJUVANT (mg) | VOLUME |
|---|---|---|---|---|---|---|
| 1 | 4 | control (IM) | nil (saline) | — | AlOH (1 mg) | 1 ml |
| 2 | 4 | IM | VacA + CagA + NAP | 250 μg each (tot. 750 μg) | AlOH (1 mg) | 1 ml |
| 3 | 4 | IM | VacA + CagA + NAP | 50 μg each (tot. 150 μg) | AlOH (1 mg) | 1 ml |
| 4 | 4 | IM | VacA + CagA + NAP | 10 μg each (tot. 30 μg) | AlOH (1 mg) | 1 ml |
| 5 | 4 | IM | CCUG lysate | 25 mg | AlOH (1 mg) | 1 ml |
| 6 | 4 | IM | CCUG lysate | 5 mg | AlOH (1 mg) | 1 ml |

What is claimed is:

1. A method of protection against infection by *H. pylori* in a human subject comprising administering intramuscularly and not mucosally to the human subject, an effective amount of a composition consisting essentially of a mixture of *H. pylori* antigens and coadministering an adjuvant, wherein the adjuvant is aluminum hydroxide, or an adjuvant composition comprising 5% squalene, 0.5% polyoxyelthylene-sorbitan monooleate and 0.5% sorbitan trioleate formulated into submicron particles.

2. The method of claim 1 wherein one or more antigens in the mixture separately or in combination elicit a protective immune response.

3. The method of claim 1, wherein the mixture comprises a virulence factor of *H. pylori*.

4. The method of claim 3, wherein the virulence factor of *H. pylori* is VacA, CagA, NAP or urease.

5. The method of claim 1, wherein the mixture comprises purified antigen(s).

6. The method of claim 1, wherein the composition further comprises one or more pharmaceutically acceptable excipients.

7. The method of claim 1, wherein the mixture comprises a whole cell immunogen.

8. The method of claim 7, wherein the whole cell immunogen is prepared by extraction from *H. pylori* cells.

9. The method of claim 8, wherein the whole cell immunogen is prepared by lysis of *H. pylori* cells.

10. The method of claim 8, wherein the whole cell immunogen is prepared by sonication of *H. pylori* cells.

11. The method of claim 7, wherein the whole cell immunogen comprises inactivated *H. pylori* cells.

12. The method of claim 7, wherein the whole cell immunogen consists of inactivated *H. pylori* cells.

13. A method for preventing *H. pylori* infection in a human subject consisting essentially of administering intramuscularly and not mucosally to the human subject, an immunologically effective amount of a composition comprising an *H. pylori* cell lysate in combination with a pharmaceutically acceptable excipient and an adjuvant, wherein the adjuvant is a composition comprising 5% squalene, 0.5% polyoxyelthylenesorbitan monooleate and 0.5% sorbitan trioleate formulated into submicron particles.

14. A method for preventing *H. pylori* infection in a human subject consisting essentially of administering intramuscularly and not mucosally to the human subject, an immunologically effective amount of a composition comprising purified *H. pylori* VacA, CagA and NAP in combination with a pharmaceutically acceptable excipient and an adjuvant, wherein the adjuvant is a composition comprising 5% squalene, 0.5% polyoxyelthylenesorbitan monooleate and 0.5% sorbitan trioleate formulated into submicron particles.

* * * * *